United States Patent
Lafyatis et al.

(10) Patent No.: US 9,365,469 B2
(45) Date of Patent: Jun. 14, 2016

(54) PROCESS FOR TRANSALKYLATING AROMATIC HYDROCARBONS

(75) Inventors: David S. Lafyatis, Schaumburg, IL (US); Edwin P. Boldingh, ArlingtonHeights, IL (US); Eric J. Baker, Chicago, IL (US); James A. Johnson, Clarendon Hills, IL (US); Robert B. Larson, Lisle, IL (US)

(73) Assignee: UOP LLC, Des Plaines, IL (US)

( * ) Notice: Subject to any disclaimer, the term of this patent is extended or adjusted under 35 U.S.C. 154(b) by 235 days.

(21) Appl. No.: 13/232,019

(22) Filed: Sep. 14, 2011

(65) Prior Publication Data

US 2013/0066123 A1    Mar. 14, 2013

(51) Int. Cl.
  *C07C 6/12*  (2006.01)
  *C07C 2/00*  (2006.01)
  *C07C 2/54*  (2006.01)

(52) U.S. Cl.
  CPC ............. *C07C 6/126* (2013.01); *C07C 2529/26* (2013.01)

(58) Field of Classification Search
  CPC ................ C07C 2/00; C07C 2/54; C07C 6/12
  USPC .................................. 585/312, 446, 449, 483
  See application file for complete search history.

(56) References Cited

U.S. PATENT DOCUMENTS

| | | | |
|---|---|---|---|
| 4,259,537 A * | 3/1981 | Chu ............................... | 585/467 |
| 4,956,511 A | 9/1990 | Butler et al. | |
| 5,321,183 A | 6/1994 | Chang | |
| 5,520,799 A | 5/1996 | Brown et al. | |
| 6,855,854 B1 | 2/2005 | James, Jr. | |
| 7,405,335 B1 * | 7/2008 | Casey et al. ................... | 585/319 |
| 7,439,204 B2 | 10/2008 | McMinn et al. | |
| 7,563,358 B2 | 7/2009 | Stavens | |
| 7,601,311 B2 | 10/2009 | Casey et al. | |
| 7,626,064 B1 * | 12/2009 | Boldingh et al. ............. | 585/475 |
| 2008/0262280 A1 | 10/2008 | Casey | |
| 2009/0036724 A1 | 2/2009 | Negiz | |

FOREIGN PATENT DOCUMENTS

| | | |
|---|---|---|
| EP | 0538229 A2 * | 9/1992 |
| WO | 2012050748 A2 | 4/2012 |

OTHER PUBLICATIONS

U.S. Appl. No. 12/894,209, filed Sep. 30, 2010, Edwin P. Boldingh.
International Search Report for PCT/US2012/051784, mailing date Feb. 21, 2013.
European search report for 12832426.6-1454 / 2755934 PCT/US201251784, Reference: MDP/P131771EP00; dated Mar. 18, 2015.

* cited by examiner

*Primary Examiner* — In Suk Bullock
*Assistant Examiner* — Youngsul Jeong

(57) ABSTRACT

The present invention is a process for transalkylating aromatic hydrocarbon compounds, the process comprising introducing an aromatic hydrocarbon feed stream into a transalkylation zone to yield high-purity benzene as a byproduct while meeting transalkylation objectives. The feed stream contacts a catalyst in the transalkylation zone under conditions adjusted to control benzene purity as well as transalkylation performance.

20 Claims, No Drawings

PROCESS FOR TRANSALKYLATING AROMATIC HYDROCARBONS

FIELD OF THE INVENTION

The present invention generally relates to improved processes for transalkylating aromatic hydrocarbon compounds. More particularly the invention relates to aromatic transalkylation processes producing xylenes and benzene.

DESCRIPTION OF RELATED ART

Xylene isomers ("xylenes") and benzene are produced in large volumes from petroleum by the reforming of naphtha. However, neither the xylenes nor benzene are produced in sufficient volume to meet demand. Consequently, other hydrocarbons are necessarily converted to increase the yield of the xylenes and benzene via processes such as transalkylation, disproportionation, isomerization, and dealkylation. For example, toluene commonly is dealkylated to produce benzene. Alternatively, or additionally, toluene can be disproportionated to yield benzene and $C_8$ aromatics from which the individual xylene isomers are recovered.

More recently, development has been directed at selectively transalkylating heavier aromatics, such as $C_9+$ aromatics, with toluene and/or benzene to increase the yield of xylenes and benzene from aromatics complexes. In this regard, a variety of catalysts have been developed for these processes. For example, a wide range of zeolites, including mordenite, have been disclosed as effective transalkylation catalysts. Shaped catalysts, multiple zeolites, metal modifiers, and treatments such as steam calcination have been described as increasing the effectiveness of the catalysts.

Known catalysts are effective for producing xylenes and benzene. Specifically, catalysts having a sufficient metal function are suitable to convert heavier aromatics, such as $C_9+$ aromatics to xylenes and benzene and provide improved catalyst stability in a transalkylation process. However, in transalkylation processes employing such catalysts, aromatic rings may become saturated or even cleaved resulting in naphthene and acyclic paraffin (non-aromatics) co-production, which can result in a loss of valuable aromatics. Also, because some of the non-aromatics have similar boiling points to benzene (benzene co-boilers), they are not readily removed to achieve a benzene product having a desired purity for commercial applications. Although the benzene co-boilers can be extracted with a solvent, such processes are expensive and typically require additional equipment.

Accordingly, it is desirable to provide a transalkylation process that produces a high-purity benzene product. Simultaneously, it is desirable to have a catalyst that exhibits a high activity and a strong resistance to coking so as to extend the time that the catalyst can be used before being replaced or regenerated. It furthermore would be highly desirable to be able to process very heavy feeds such as those containing the residual components as would come from unfractionated xylene column bottoms thereby further increasing xylene yield while still maintaining a high activity and a strong resistance to coking, so as to achieve a long catalyst life while achieving a high purity benzene product throughout the catalyst life. Catalysts that have the high stability and activity to attain a long catalyst life while processing heavy feeds such as those containing the residual components as would come from unfractionated xylene column bottoms under standard transalkylation conditions intrinsically will have difficulty in achieving high benzene purity at those same conditions early in its lifetime. Thus, a highly desirable feature of this invention is to provide an operating methodology that will allow all three aims of processing very heavy feed components whilst achieving a long catalyst lifetime and a high benzene purity throughout the entire run to be met. Thus, this invention provides a unique operating methodology to permit these aims to be met simultaneously.

Other desirable features and characteristics of the present invention will become apparent from the subsequent detailed description of the invention and the appended claims.

SUMMARY OF THE INVENTION

High activity and stability transalkylation catalysts such as proposed here for transalkylation tend to produce benzene co-boilers particularly during lower-severity conditions of normal operation during early portions of the process cycle, resulting in unacceptable benzene product purity. However, it has been discovered that initial operation during the early period of a process cycle at benzene-purity-directed conditions, whilst resulting in somewhat more rapid catalyst deactivation, also reduces the production of benzene co-boilers and better enables their destruction with concomitant enabling of acceptable purity of the benzene fraction of the transalkylation reaction product stream. The invention thus enables control of the amount of benzene co-boilers and the resulting purity of a benzene product stream recovered after distillation to separate the products during early parts of the process cycle, so that even high activity and stability transalkylation catalysts may meet benzene purity requirements.

In a broad embodiment, the invention is a process for transalkylating aromatic hydrocarbon compounds while maintaining the purity of a benzene product during an operating cycle comprising two or more portions of the cycle under differing transalkylation conditions, the process comprising: introducing a feed stream comprising the aromatic hydrocarbon compounds to a transalkylation zone containing a catalyst comprising an aluminosilicate zeolite component having an MOR framework type, optionally one or more additional aluminosilicate zeolite components, an inorganic oxide binder, and a metal component; contacting the feed stream with the catalyst in the transalkylation zone under benzene-purity-directed transalkylation conditions during an initial portion of the operating cycle; contacting the feed stream with the catalyst in the transalkylation zone under standard transalkylation conditions in a latter portion of the operating cycle; and, producing a reaction product stream comprising xylenes and a high-purity benzene fraction.

A more specific embodiment is a process for transalkylating aromatic hydrocarbon compounds while maintaining the purity of a benzene product during an operating cycle comprising two or more portions of the cycle under differing transalkylation conditions, the process comprising: introducing a feed stream comprising the aromatic hydrocarbon compounds to a transalkylation zone containing a catalyst comprising an aluminosilicate zeolite component having an MOR framework type, optionally one or more additional aluminosilicate zeolite components, an inorganic oxide binder, and a metal component; contacting the feed stream with the catalyst in the transalkylation zone during an initial portion of the operating cycle under benzene-purity-directed transalkylation conditions comprising one or more of higher operating temperature, lower operating pressure and lower hydrogen-to-hydrocarbon ratio relative to standard transalkylation conditions effective during a latter portion of the operating cycle; contacting the feed stream with the catalyst in the transalkylation zone under standard transalkylation conditions in the latter portion of the operating cycle; and, producing a reaction product stream comprising xylenes and a high-purity benzene fraction.

A yet more specific embodiment is a process for transalkylating aromatic hydrocarbon compounds while maintaining the purity of a benzene product during an operating cycle comprising two or more portions of the cycle under differing transalkylation conditions, the process comprising: introducing a feed stream comprising the aromatic hydrocarbon compounds to a transalkylation zone containing a catalyst comprising an aluminosilicate zeolite component having an MOR framework type, optionally one or more additional aluminosilicate zeolite components, an inorganic oxide binder, and a metal component; contacting the feed stream with the catalyst in the transalkylation zone during an initial portion of the operating cycle under benzene-purity-directed operating conditions comprising one or more of higher operating temperature, lower operating pressure and lower hydrogen-to-hydrocarbon ratio relative to standard transalkylation conditions effective during a latter portion of the operating cycle; transitioning the processing conditions gradually from benzene-purity-directed conditions to standard transalkylation conditions during the initial portion of the process cycle; contacting the feed stream with the catalyst in the transalkylation zone under standard transalkylation conditions in the latter portion of the operating cycle; and producing a reaction product stream comprising xylenes and a high-purity benzene fraction.

Benzene-purity-directed operating conditions are applied to produce a product stream that achieves a benzene purity of at least 99.9% benzene by distillation during an initial portion of the process cycle. Then, during the latter portion of the operating cycle after the catalyst has deactivated to a level where it can produce a product stream that achieves this benzene purity by mere fractionation at standard transalkylation conditions, reaction conditions are adjusted to milder conditions so that the lifetime of the catalyst may be maximized. Thus a satisfactory lifetime of the catalyst is maintained while producing a reaction product stream comprising xylenes and high-purity benzene over the entire process cycle.

DETAILED DESCRIPTION

The aromatic hydrocarbons to be transalkylated by processes of the invention include alkylaromatic hydrocarbons of the general formula $C_6H_{(6-n)}R_n$, where n is an integer from 0 to 5 and R is $CH_3$, $C_2H_5$, $C_3H_7$, or $C_4H_9$, in any combination. Non-limiting examples include: benzene, toluene, ethylbenzene, ethyltoluenes, propylbenzenes, tetramethylbenzenes, ethyl-dimethylbenzenes, diethylbenzenes, methylethylbenzenes, methylpropylbenzenes, ethylpropylbenzenes, triethylbenzenes, trimethylbenzenes, di-isopropylbenzenes, other $C_9$ and heavier aromatic compounds, and mixtures thereof. The feed stream may comprise lower levels of ortho-xylene, meta-xylene, and para-xylene than are desired products of the process, thus enabling a product isomer ratio more closely meeting product requirements.

As used herein, the term "transalkylation" encompasses transalkylation between and among alkyl aromatics, between benzene and alkyl aromatics, and it includes dealkylation and disproportionation, e.g., of toluene to benzene and xylene. The aromatic hydrocarbons also may comprise naphthalene and other $C_{10}$ and $C_{11}$ and higher aromatics. Herein, hydrocarbon molecules may be abbreviated $C_1$, $C_2$, $C_3$, . . . $C_n$, where "n" represents the number of carbon atoms in the hydrocarbon molecule. Such abbreviations followed by a "+" is used to denote that number of carbon atoms or more per molecule, and a "−" is used to denote that number of carbon atoms or less per molecule.

Polycyclic aromatics having from 2 to 4 rings are permitted in the feed stream of the present invention. Non-limiting examples include: indanes, naphthalenes, tetralins, decalins, biphenyls, diphenyls and fluorenes.

The aromatic hydrocarbons to be transalkylated may be introduced to the transalkylation zone in one or more feed streams. As used herein, the term "zone" can refer to one or more equipment items and/or one or more sub-zones. Equipment items may include, for example, one or more vessels, heaters, separators, exchangers, conduits, pumps, compressors, and controllers. Additionally, an equipment item can further include one or more zones or sub-zones. In embodiments having multiple feed streams, the feed streams may be introduced separately to the transalkylation zone, or two or more of the feed streams may be combined in any manner prior to passing them into the transalkylation zone.

The feed streams may be derived from one or more sources including, without limitation, catalytic reforming, pyrolysis of naphtha, distillates or other hydrocarbons to yield light olefins and heavier aromatics-rich byproducts, and catalytic or thermal cracking of heavy oils to yield products in the gasoline range. Products from pyrolysis or other cracking operations generally will be hydrotreated according to processes well known in the industry before being charged to the transalkylation zone in order to remove sulfur, olefins and other compounds which would affect product quality. Light cycle oil also may be beneficially hydrocracked to yield lighter components which can be reformed catalytically to yield the aromatics-rich feed stream. If the feed stream is catalytic reformate, the reformer preferably is operated at high severity for high aromatics yield with a low concentration of non-aromatics in the product. The reformate may also be subjected to olefin saturation to remove potential product contaminants and materials that could polymerize to heavy non-convertibles in a transalkylation process. Such processing steps are described in U.S. Pat. No. 6,740,788 B1, which is incorporated herein by reference thereto.

A feed stream can include a substantially pure alkylaromatic hydrocarbon of from about 6 to about 15 carbon atoms, a mixture of such alkylaromatic hydrocarbons, or a hydrocarbon fraction rich in said alkylaromatics. A feed stream also may contain lesser concentrations of non-aromatics such as pentanes, hexanes, heptanes and heavier paraffins along with paraffins along with methylcyclopentane, cyclohexane and heavier naphthenes; pentanes and lighter paraffins generally will have been removed before processing. The combined transalkylation feed preferably contains no more than about 10 wt % non-aromatics; and olefins preferably are restricted to a Bromine Index of no more than about 1000, and more preferably to no more than about 500.

In an optional embodiment, at least two feed streams are introduced to the transalkylation zone, a light feed stream and a heavy feed stream. The light aromatic feed stream may comprise at least one of benzene and toluene. Preferred components of the heavy aromatic feed are $C_9$+ aromatics, thereby effecting transalkylation of toluene and $C_9$+ aromatics to yield additional xylenes. Benzene may also be transalkylated to yield additional toluene. Indane may be present in the heavy aromatics feed stream although it is not a desirable component to effect high yields of xylenes in the transalkylation zone effluent. $C_{10}$+ aromatics also may be present, preferably in an amount of 30% or less of the heavy aromatic feed. The heavy aromatic feed stream preferably comprises at least about 90 mass % aromatics, and may be derived from the same or different known refinery and petrochemical processes as the benzene/toluene feed stream and/or may be recycled from the separation of the transalkylation effluent.

The aromatic feed to a transalkylation reaction zone is usually first heated by indirect heat exchange against the reaction product stream and then is heated to reaction temperature by exchange with a warmer stream, steam or a furnace. The feed is preferably transalkylated in the vapor phase and in the presence of hydrogen. In an embodiment a hydrogen stream is introduced to the transalkylation zone. The hydrogen stream may comprise other compounds, e.g. $C_1$ to $C_4$ hydrocarbons, in addition to hydrogen. Hydrogen and hydrocarbons may be recycled in the process as described below. If present, free hydrogen is associated with the feedstock and recycled hydrocarbons, if any, in an amount from about 0.1 moles per mole of aromatics up to 10 moles per mole of aromatics. This ratio of hydrogen to aromatics is also referred to as hydrogen to hydrocarbon ratio.

The feed then is passed through one or more reactors containing the transalkylation catalyst to produce a reaction product stream comprising unconverted feed and product hydrocarbons including xylenes and benzene. This reaction product stream is normally cooled by indirect heat exchange against the aromatic feed stream entering the transalkylation zone and may be further cooled through the use of air or cooling water. The reaction product stream may be separated e.g. in a vapor-liquid separator to produce a vapor phase hydrogen stream and a liquid phase reaction product stream. The vapor phase hydrogen stream includes hydrogen and light hydrocarbons which may be recycled and combined with the feed as described above. The liquid phase reaction product stream may be passed into a stripping column in which substantially all $C_5$ and lighter hydrocarbons present are concentrated into an overhead stream and removed from the process. As used herein, the term "substantially all" means an amount generally of at least 90%, preferably at least 95%, and optimally at least 99%, by weight, of a compound or class of compounds in a stream. The stripping column also produces a net stripper bottoms stream, which is referred to herein as the transalkylation zone effluent.

The transalkylation zone effluent may be further separated in a distillation zone comprising at least one distillation column to produce a benzene product stream. Various flow schemes and combinations of distillation columns to separate transalkylation zone effluent via fractional distillation are well known in the art. In addition to the benzene product stream, the distillation zone may produce a toluene product stream and a $C_8+$ product stream. See, e.g., U.S. Pat. No. 7,605,295. It is also known that the transalkylation zone stripper column may be designed and operated to produce a benzene product stream. See, e.g., U.S. Pat. No. 6,740,788. Thus, the reaction product stream contains a benzene fraction that may be separated by fractional distillation to produce a benzene product stream. A benzene product of acceptable purity according to the present invention is benzene which generally would meet specifications for further chemical processing merely by fractional distillation of the reaction products, preferably, without limitation, having a purity of at least about 99.9% by weight.

In another embodiment, the transalkylation effluent is separated into a light recycle stream, a mixed $C_8$ aromatics product, and a heavy aromatic product stream in a distillation zone. The mixed $C_8$ aromatic product may be sent for recovery of para-xylene and/or other isomers. The light recycle stream may be diverted to other uses such as benzene and toluene recovery, but may be recycled, in part, to the transalkylation zone. The heavy recycle stream contains substantially all of the $C_9$ and heavier aromatics and may be partially or totally recycled to the transalkylation reaction zone.

The aromatic feed stream introduced into the transalkylation zone contacts the catalyst at transalkylation conditions to produce the reaction product stream which comprises unconverted feed, xylenes, and benzene. As used herein the term "benzene co-boilers" means non-aromatic hydrocarbon compounds having 6 or 7 carbon atoms per molecule. Benzene co-boilers that are particularly difficult to separate from benzene by fractional distillation include cyclohexane; methylcyclopentane; 2,3-dimethylpentane; 3-methylhexane; and dimethylcyclopentane.

A process cycle runs from the initial introduction of feed until the process is discontinued to regenerate or replace the catalyst. A process cycle may be measured in a variety of ways including: time on stream (i.e. time feed is being introduced); the quantity of feed that has been introduced, e.g. mass or volume of feed processed; and the quantity of feed (mass or volume) per quantity of catalyst (mass or volume), e.g. barrels (feed) per pound (catalyst) (BPP), cubic meters of feed (e.g. at standard or normal conditions) per mass or volume of catalyst. A process cycle may be temporarily suspended or halted by discontinuing feed introduction. If suspended for an extended period of time, the unit may be held in a stand-by mode. However, the length of the process cycle will continue to accrue once feed introduction resumes, provided the catalyst has not been regenerated or replaced.

During an initial portion of the process cycle, the catalyst usually exhibits the highest activity; therefore, the operating temperatures are usually at a minimum needed to effect the transalkylation reaction. "Standard" transalkylation conditions of temperature, pressure, hydrogen purity and hydrogen circulation, chosen to optimize the transalkylation reaction while maintaining catalyst activity and avoid deactivation, typically result in higher amounts of benzene co-boilers and thus the lowest benzene purity experienced over the process cycle generally occurs during this initial period. The catalyst ages and its transalkylation activity deactivates as the process cycle continues, and to maintain the desired level of feed conversion the reactor temperature usually is increased. Without wishing to be bound by any particular theory, it has been found that benzene co-boilers are cracked more efficiently by the acid sites on the catalyst, especially by MFI zeolite if included in the catalyst formulation, at higher temperatures. Thus, as the process cycle continues, the benzene product purity is typically noted to improve as the operating temperature is increased. It is notable that benzene co-boilers also tend to be formed to a lesser extent at lower pressures and hydrogen-to-hydrocarbon ratios.

Benzene purity may be controlled during the initial portion of the process cycle, when purity at standard transalkylation conditions may be low, by imposing higher-severity benzene-purity-directed transalkylation conditions comprising one or more of higher temperature, lower pressure, or lower hydrogen-to-hydrocarbon ratio. Such conditions will tend to increase the catalyst deactivation rate, but the value of the benzene product of acceptable purity is considered to justify such deactivation during the initial portion of the process cycle. Without so restricting the invention, benzene-purity-directed transalkylation conditions during the initial portion of the process cycle typically are imposed during no more than about 50% of the process cycle, usually from about 1% to 25% and more usually from about 2% to 10% of the process cycle. The process cycle and the relative fractions thereof devoted to benzene-purity-directed and standard transalkylation conditions are determined on the basis of mass of feed per mass of catalyst, e.g. metric ton of feed per metric ton of catalyst.

Rather than a single step change between benzene-purity-directed conditions and standard transalkylation conditions, processing conditions preferably are transitioned gradually during the initial portion of the process cycle to minimize catalyst deactivation while maintaining benzene purity. For example, without limitation, one or more of the following gradual changes may be made from time to time while operating at benzene-purity-directed conditions:

Temperature: about 0.5 to 10° C.
Pressure: about 10 to 500 kPa
Hydrogen/hydrocarbon mole ratio: about 0.05 to 0.5

Another approach would be for adjustments to be made to the variables temperature, pressure and hydrogen/hydrocarbon mole ratio by an automatic controller, using the benzene purity measured for example in one or more of the reaction product stream, the transalkyation zone effluent stream, and the benzene product stream as a feedback signal to a controller. In this case, changes to these variables might be made at frequent time intervals (such as hourly or daily); changes to a variable made by the automatic controller thus might be smaller than described in the ranges above.

Benzene-purity-directed transalkylation conditions are terminated when the benzene product purity requirement is met at standard transalkylation conditions, i.e., transalkylation conditions optimized to maintain activity and minimize catalyst deactivation. Benzene purity may be determined by analysis of the benzene product stream and/or from a determination of the amount of benzene co-boilers relative to the amount of benzene. Benzene co-boilers comprise hydrocarbons which cannot completely and effectively be separated from benzene by distillation, for example 6- and 7-carbon naphthenes and paraffins as described earlier. "High-purity benzene fraction" is assessed in terms of the ratio of benzene to these co-boilers, i.e., the purity of benzene recovered by conventional fractionation in an aromatics complex to separate toluene. The amount of benzene co-boilers relative to the amount of benzene may be determined for example in any of the reaction product stream, the transalkylation zone effluent stream, and the benzene product stream. The determination of benzene purity and the relative amount of the benzene co-boilers may be performed by manually obtaining samples and analyzing them off-line or by automatic on-line analysis. The manual and automatic modes of these steps may be combined in any manner. For example, an on-line analyzer may determine the amount of benzene co-boilers relative to the amount of benzene in the reaction product stream and send a signal to a process controller. The process controller may in turn send a signal to a controller that regulates the adjustment of the process conditions. Algorithms, such as to convert the relative amount of co-boilers to a purity of the benzene product steam may include terms to account for the fractional distillation efficiency and/or time lags in the process, and may be applied in or by any of the analyzer, controller, and control valve to generate or interpret the signals. Such techniques are well known in the art of process control.

Contacting the feed with the catalyst can be effected in any conventional or otherwise convenient manner and may occur as a batch or continuous type of operation. In an embodiment, the catalyst is disposed in one or more fixed beds in a reaction zone of a vertical reactor with the aromatic feed and sulfur charged through the bed in an upflow or downflow manner. Transalkylation conditions may include a temperature in a range of from about 200° C. to about 540° C., preferably between about 200° C. to about 480° C.; a pressure in a range of from about 100 kPa to about 6 MPa absolute, and a weight hourly space velocity (WHSV, i.e., weight of aromatic feed introduced per weight of catalyst per hour) in a range of from about 0.1 to about 20 hr−1.

The invention preferably comprises a transalkylation catalyst comprising: an aluminosilicate zeolite having an MOR framework type, optionally one or more additional aluminosilicate zeolite components, a metal component comprising a metal selected from the group consisting of nickel, cobalt, molybdenum, tungsten, tin, germanium, lead, indium, rhenium, platinum, palladium, and combinations thereof, and an inorganic oxide binder.

Aluminosilicate zeolite having an MOR framework is described in Atlas of Zeolite Framework Types, 6th Revised Edition, C. H. Baerlocher, L. B. McCusker, and D. H. Olson, editors, Elsevier (2007), pp. 218-219. The MOR framework comprises four- and five-membered rings of $SiO_1$ and $AlO_4$ tetrahedra to form a crystal lattice comprising 12-ring channels running parallel along a crystal axis to give a tubular configuration. In an embodiment, the aluminosilicate zeolite having an MOR framework comprises mordenite. Where mordenite is a component of the catalyst, the mordenite preferably has a $Si/Al_2$ molar ratio of less than about 40. The $Si/Al_2$ molar ratio of mordenite in an embodiment is less than about 25, and in another embodiment the mordenite $Si/Al_2$ molar ratio is between about 15 and about 25. Mordenite may be synthesized with a $Si/Al_2$ molar ratio of between about 10 and about 20. Mordenite is preferably at least partially in the hydrogen form and/or may be dealuminated by a variety of techniques, e.g. steaming, and acid extraction of aluminum to increase the $Si/Al_2$ ratio of the mordenite.

In a preferred embodiment, the aluminosilicate zeolite having an MOR framework comprises UZM-14. UZM-14 is described in U.S. Pat. No. 7,687,423, which is incorporated herein by reference in its entirety. UZM-14 comprises globular aggregates of crystallites having a MOR framework type comprising 12-ring channels, and one or more of the following distinctive characteristics: a mesopore volume of at least about 0.10 cc/gram, preferably at least about 0.13 cc/gram, more preferably at least about 0.2 cc/gram; a mean crystallite length parallel to the direction of the 12-ring channels of about 60 nm or less, preferably about 50 nm or less; a $Si/Al_2$ mole ratio of between about 8 and about 50, and preferably is no more than about 30; and at least about 1×1019 12-ring channel openings per gram of UZM-14 material.

In one embodiment, UZM-14 comprises globular aggregates of crystallites having a MOR framework type comprising 12-ring channels, a silica-alumina mole ratio of from about 8 to no more than about 30, a mesopore volume of at least about 0.10 cc/gram, and a mean crystallite length parallel to the direction of the 12-ring channels of about 60 nm or less.

UZM-14 has an empirical composition in the as-synthesized form on an anhydrous basis expressed by the empirical formula:

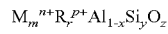

$$M_m^{n+}R_r^{p+}Al_{1-x}Si_yO_z$$

where M is at least one exchangeable cation and is selected from the group consisting of alkali and alkaline earth metals including but not limited to lithium, sodium, potassium, rubidium, cesium, calcium, strontium, barium and mixtures thereof. R is at least one organic cation selected from the group consisting of protonated amines, protonated diamines, quaternary ammonium ions, diquaternary ammonium ions, protonated alkanolamines, and quaternized alkanolammonium ions. Relating the components, "m" is the mole ratio of M to Al and varies from about 0.05 to about 0.95; "r" is the mole ratio of R to Al and has a value of about 0.05 to about 0.95; "n" is the weighted average valence of M and has a value of about 1 to about 2; "p" is the weighted average valence of R and has a value of about 1 to about 2; "y" is the mole ratio of Si to Al and varies from about 3 to about 50; and "z" is the mole ratio of O to Al and has a value determined by the equation:

$$z=(m \cdot n + r \cdot p + 3 + 4y)/2.$$

In a preferred embodiment, the one or more additional aluminosilicate zeolite components comprises an MFI zeolite having a Si/Al2 molar ratio of less than 80. Such zeolites having an MFI type framework are described in *Atlas of Zeolite Framework Types,* 6th Revised Edition, C. H. Baerlocher, L. B. McCusker, and D. H. Olson, editors, Elsevier (2007). In an embodiment, MFI molecular sieves optionally used in the catalysts of this invention have a Si/Al$_2$ molar ratio of less than about 40, preferably less than about 25, for example, between about 15 to about 25. An example of a suitable MFI molecular sieve for inclusion in the catalyst includes, but is not limited to, ZSM-5, which is disclosed in U.S. Pat. No. 3,702,886, incorporated herein, by reference thereto. Suitable MFI molecular sieves are available, for example, from Zeolyst International of Conschocken, Pa. and Tosoh Corporation of Tokyo, Japan.

The inorganic oxide binder of the catalyst comprises such materials as alumina, silica, zirconia, titania, thoria, boria, magnesia, chromia, stannic oxide, and the like as well as combinations and composites thereof, for example silica-alumina, alumina-zirconia, alumina-titania, aluminum phosphate, and the like. Alumina is a preferred refractory inorganic oxide binder. As is well known in the art, a precursor of the desired refractory inorganic oxide may be used to form, bind, and/or otherwise prepare the catalyst. Such binder precursors or sources may be converted into a refractory inorganic oxide binder, e.g. by calcination. The alumina may be any of the various aluminum oxides, hydroxides, and gels, including boehmite, pseudo-boehmite, gibbsite, bayerite, and the like, especially transition and gamma aluminas. Suitable aluminas are commercially available, e.g. under the trade names CATAPAL B and VERSAL 250.

The metal component of the catalyst comprises a metal selected from the group consisting of nickel, cobalt, molybdenum, tungsten, tin, germanium, lead, indium, rhenium, platinum, palladium, and combinations thereof. In an embodiment, the metal component comprises a metal selected from the group consisting of nickel, cobalt, molybdenum, tungsten, rhenium, platinum, palladium, and combinations thereof. In an embodiment the metal content of the catalyst ranges from about 0.01 wt % to about 10.0 wt % as the metal based upon the total weight of the catalyst.

The metal component may be incorporated into the catalyst in any suitable manner such as comulling, coprecipitation or cogellation with the carrier material, ion exchange, or impregnation. The metal component may exist within the final catalyst as a compound such as an oxide, sulfide, halide, or oxyhalide, in chemical combination with one or more of the other ingredients of the composite, or as an elemental metal. One method of preparing the catalyst involves the use of a water-soluble or solvent-soluble, decomposable compound of the metal to impregnate the molecular sieve-containing support. Alternatively, a metal compound may be added at the time of compositing the molecular sieve component and binder.

The weight ratio of the optional MFI molecular sieve component, if present, to the aluminosilicate zeolite having the MOR framework may range from about 1:10 to 5:1. In an embodiment, the aluminosilicate zeolite component having the MOR framework comprises from about 20 wt % to about 80 wt % of the catalyst, the MFI molecular sieve component comprises from about 10 wt % to about 70 wt % of the catalyst, and the inorganic oxide binder comprises between about 1 wt % and about 40 wt % of the catalyst.

The catalyst may optionally include one or more additional aluminosilicate zeolite components preferably selected from one or more of MFI, MEL, EUO, FER, MFS, MTT, MTW, MWW, MAZ, TON and FAU (IUPAC Commission on Zeolite Nomenclature) and UZM-8 (see U.S. Pat. No. 6,756,030 which is herein incorporated by reference in its entirety). The catalyst may optionally include a fluoride component in an amount ranging from about 0.1 wt % to about 5.0 wt % of fluoride based upon the total weight of the catalyst. The fluoride component may be incorporated into the catalyst by any known technique, e.g. impregnation.

The techniques used to prepare the catalyst are well known to those of ordinary skill in the art. The catalyst can be formed by combining the aluminosilicate zeolite component having the MOR framework, one or more optional additional aluminosilicate zeolite components, and the inorganic oxide binder and/or a precursor thereof in any conventional or otherwise convenient manner to form spheres, pills, pellets, granules, extrudates, or other suitable particle shapes. For example, finely divided aluminosilicate zeolite having the MOR framework and MFI molecular sieve particles, and metal salt particles can be dispersed in an alumina sol, and the mixture in turn dispersed as droplets in a hot oil bath whereby gelation occurs with the formation of spheroidal gel particles. A preferred method comprises mixing a finely divided form of the selected aluminosilicate zeolite having the MOR framework, MFI molecular sieve particles, a binder and/or precursor thereof, with a metal salt and, optionally, a lubricant; and compressing the mixture into pills or pellets. Alternatively, and still more preferably, the aluminosilicate zeolite having the MOR framework, MFI molecular sieve particles, binder and/or precursor thereof, and metal salt are combined and admixed with a peptizing agent in a mixer-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobes, with a trilobe form being favored. The extrudates also may be formed into spheres by means of a spinning disc or drum. The variously formed particles are then usually dried and/or calcined.

If the metal component is not included in the above forming steps, or if an additional metal component is to be included, the formed particles produced above can be impregnated with a soluble, decomposable compound containing the metal component to form a composite. For example, when the metal component comprises molybdenum, typical compounds which may be employed include ammonium heptamolybdate, alkali metal molybdates (also peroxo-, di-, tri-, tetra-, hepta-, octa-, or tetradecamolybdate), molybdic acid, phosphomolybdic acid, Mo—P heteropolyanion compounds, acetyl acetonates, Mo(0) metal, Mo oxides, Mo peroxo complexes, and mixtures thereof. The composite is preferably calcined in an air atmosphere at a temperature of from about 425° C. to about 750° C., preferably at a temperature of from about 475° C. to about 600° C., over a period of from about 0.5 to about 10 hours. Typically, the formed particles are also calcined at similar conditions prior to the impregnation step.

The catalyst preparation may include various optional steps such as drying and steaming which are well known in the art.

Example 1

A catalyst was prepared according to the procedures described in U.S. Pat. No. 7,626,064 B1 and was tested for aromatics transalkylation following a standard transalkylation testing procedure. Prior to testing, the catalyst was sulfided in-situ as is well known in the art to convert the $MoO_3$ of the calcined catalyst, at least partially, to molybdenum sulfide. The feedstock to the test comprised aromatics in essentially the following proportions by weight:

| | |
|---|---|
| Toluene | 50% |
| $C_9$ aromatics | 38% |
| $C_{10}$ aromatics | 10% |
| $C_{11+}$ aromatics | 1.5% |

Example 2

The test was controlled to maintain a constant conversion level of 50% by weight of feed at a weight hourly space velocity of 3.0 grams of HCBN feed/gram of catalyst-hour. The test was carried out past a catalyst life of 5 barrels of feed per pound of catalyst, wherein standard transalkylation conditions were applied at the initial (0-0.7) and final stages (5+) of the experiment for conversion of the feedstock. In the following table, "BPP" indicates barrels of feed processed per pound of catalyst and thus the period in the operating cycle, "0" being the start of the cycle. "Temp" is the weighted average bed temperature in ° C. for the operating period. "Press" is the operating pressure in MPa. "H2/HC" is the mole ratio of hydrogen to feedstock hydrocarbons. "Purity" is the mole % H2 in the recycle hydrogen. "DAR" is the deactivation rate in ° C. per BPP, required to maintain the conversion level at 50%. Product benzene purity is indicated as "% Benzene." Weight hourly space velocity was maintained at 3 throughout the cycle.

| BPP | Temp | Press | H2/HC | Purity | DAR | % Benzene |
|---|---|---|---|---|---|---|
| 0.0-0.7 | 347 | 2.9 | 3.0 | 92% | * | 99.77% |
| 1.1-2.0 | 366 | 2.2 | 2.0 | 83% | 5.5 | 99.94% |
| 2.4-3.1 | 370 | 2.9 | 1.0 | 86% | 5.1 | 99.93% |
| 3.7-4.4 | 379 | 1.7 | 3.0 | 90% | 1.3 | 99.93% |
| 5+ | 362 | 2.9 | 3.0 | 92% | <0.4 | 99.91% |

* Initial operation: no meaningful figure

The results show that benzene does not meet the desired benzene purity during a first portion of the process cycle at standard transalkylation conditions. Conditions of temperature, pressure and hydrogen/hydrocarbon ratio at 0-0.7 BPP and at 5+ BPP are consistently less severe, directed toward effective transalkylation, resulting in the benzene purity early in the cycle (0-0.7 BPP) at 99.77% that is far below a specification of 99.9%. During the interim period between 0.7 BPP and 4.4 BPP, the benzene purity is improved to meet the desired specification through benzene-purity-directed transalkylation conditions by one or more of increasing temperature, reducing pressure and reducing hydrogen/hydrocarbon ratio. The yield of main products xylene and benzene are also maintained at an acceptable level during these benzene-purity-directed conditions. At 5+ BPP when conditions revert to standard transalkylation conditions, the operating temperature to maintain 50% conversion has increased by 15° C. relative to the initial stages of the run, due to catalyst deactivation. Therefore, the benzene purity now meets desired level of 99.9+% at these standard transalkylation conditions. The deactivation rate (DAR) is also quite low at these standard transalkylation conditions, ensuring a long catalyst lifetime, even in the challenging feedstock defined in Example 1 containing 1.5% A11+ components.

The invention claimed is:

1. A process for transalkylating aromatic hydrocarbon compounds while maintaining the purity of a benzene product during an operating cycle comprising two or more portions of the cycle under different transalkylation conditions, the process comprising:
   a. introducing a feed stream comprising the aromatic hydrocarbon compounds consisting essentially of toluene and C9+ aromatics to a transalkylation zone containing a catalyst comprising an aluminosilicate zeolite component having an MOR framework, one or more additional aluminosilicate zeolite components comprising an WI framework, an inorganic oxide binder, and a metal component comprising molybdenum;
   b. contacting the feed stream with the catalyst in the transalkylation zone under benzene-purity-directed transalkylation conditions during an initial portion of the operating cycle;
   c. contacting the feed stream with the catalyst in the transalkylation zone under standard transalkylation conditions in a latter portion of the operating cycle; and,
   d. producing a reaction product stream comprising xylenes and a high-purity benzene fraction,
   wherein the benzene-purity-directed transalkylation conditions comprise lower operating pressure relative to the standard transalkylation conditions during the latter portion of the operating cycle.

2. The process of claim 1 wherein the metal component further comprises a metal or metals selected from the group consisting of tin, germanium, indium, rhenium, platinum, palladium, and combinations thereof.

3. The process of claim 1 wherein the benzene-purity-directed transalkylation conditions comprise a higher operating temperature relative to the standard transalkylation conditions during the latter portion of the operating cycle.

4. The process of claim 1 wherein the high-purity benzene fraction comprises at least 99.9% benzene by weight.

5. The process of claim 1 further comprising separating the reaction product stream to produce a benzene product stream comprising at least 99.9% benzene by weight.

6. The process of claim 1 wherein the benzene-purity-directed transalkylation conditions are applied during no more than about 50% of the operating cycle.

7. The process of claim 6 wherein the benzene-purity-directed transalkylation conditions are applied during no more than about 25% of the operating cycle.

8. A process for transalkylating aromatic hydrocarbon compounds while maintaining the purity of a benzene product during an operating cycle comprising two or more portions of the cycle under different transalkylation conditions, the process comprising:
   a. introducing a feed stream comprising the aromatic hydrocarbon compounds comprising at least 38% C9+ aromatics to a transalkylation zone containing a catalyst comprising an aluminosilicate zeolite component having an MOR framework, an inorganic oxide binder, and a metal component;
   b. contacting the feed stream with the catalyst in the transalkylation zone during an initial portion of the operating cycle under benzene-purity-directed transalkylation conditions comprising a higher operating temperature relative to standard transalkylation conditions effective during a latter portion of the operating cycle; and c. contacting the feed stream with the catalyst in the transalkylation zone under standard transalkylation conditions in the latter portion of the operating cycle;

d. producing a reaction product stream comprising xylenes and a high-purity benzene fraction, wherein operating temperature is decreased gradually from about 0.5 to about 10° C. during the initial portion of the operating cycle.

9. The process of claim 8 wherein the catalyst further comprises one or more additional aluminosilicate zeolite components.

10. The process of claim 8 further comprising separating the reaction product stream to produce a benzene product stream comprising at least 99.9% benzene by weight.

11. The process of claim 8 wherein the benzene-purity-directed transalkylation conditions are applied during no more than 50% of the operating cycle.

12. A process for transalkylating aromatic hydrocarbon compounds while maintaining the purity of a benzene product during an operating cycle comprising two or more portions of the cycle under different transalkylation conditions, the process comprising:
   a. introducing a feed stream comprising the aromatic hydrocarbon compounds comprising C9+ aromatics to a transalkylation zone containing a catalyst comprising an aluminosilicate zeolite component having an MOR framework, an inorganic oxide binder, and a metal component;
   b. contacting the feed stream with the catalyst in the transalkylation zone during an initial portion of the operating cycle under benzene-purity-directed transalkylation conditions comprising one or more of higher operating temperature and lower operating pressure relative to standard transalkylation conditions effective during a latter portion of the operating cycle;
   c. transitioning processing conditions gradually from the benzene-purity-directed transalkylation conditions to the standard transalkylation conditions during the initial portion of the operating cycle by including at least one of decreasing operating temperature from about 0.5 to about 10° C. and increasing operating pressure from about 10 to about 500 kPa;
   d. contacting the feed stream with the catalyst in the transalkylation zone under the standard transalkylation conditions in the latter portion of the operating cycle; and
   e. producing a reaction product stream comprising xylenes and a high-purity benzene fraction,
   wherein the standard transalkylation conditions and the benzene-purity-directed transalkylation conditions include a pressure of 2.9 MPa or less.

13. The process of claim 12 wherein the catalyst further comprises one or more additional aluminosilicate zeolite components comprising an MFI framework zeolite having a $Si/Al_2$ molar ratio of less than 80.

14. The process of claim 12 further comprising separating the reaction product stream to produce a benzene product stream comprising at least 99.9% benzene by weight.

15. The process of claim 12 wherein the benzene-purity-directed transalkylation conditions are applied during no more than 50% of the operating cycle.

16. The process of claim 1 wherein the standard transalkylation conditions and the benzene-purity-directed transalkylation conditions include a pressure of 2.9 MPa or less.

17. The process of claim 8 wherein the standard transalkylation conditions and the benzene-purity-directed transalkylation conditions include a pressure of 2.9 MPa or less.

18. The process of claim 1 wherein the benzene-purity-directed transalkylation conditions include at least one of reducing operating pressure to 2.2 MPa or less and increasing operating temperature to 362° C. or more.

19. The process of claim 1 wherein the benzene-purity-directed transalkylation conditions comprise a lower hydrogen-to-hydrocarbon ratio relative to the standard transalkylation conditions during the latter portion of the operating cycle.

20. The process of claim 1 wherein the benzene-purity-directed transalkylation conditions comprise lower operating pressure, higher operating temperature, and lower hydrogen to hydrocarbon ratio relative to the standard transalkylation conditions during the latter portion of the operating cycle.

\* \* \* \* \*